(12) United States Patent
Chorpenning et al.

(10) Patent No.: US 12,083,331 B2
(45) Date of Patent: Sep. 10, 2024

(54) BLOOD PUMP ALGORITHM FOR PREVENTING AND RESOLVING LEFT VENTRICULAR SUCTION THROUGH DYNAMIC SPEED RESPONSE

(71) Applicant: HeartWare, Inc., Miami Lakes, FL (US)

(72) Inventors: Katherine Chorpenning, Miami Lakes, FL (US); Carlos Reyes, Davie, FL (US)

(73) Assignee: HeartWare, Inc., Miami Lakes, FL (US)

(*) Notice: Subject to any disclaimer, the term of this patent is extended or adjusted under 35 U.S.C. 154(b) by 103 days.

(21) Appl. No.: 17/010,077

(22) Filed: Sep. 2, 2020

(65) Prior Publication Data

US 2021/0093762 A1    Apr. 1, 2021

Related U.S. Application Data

(60) Provisional application No. 62/906,294, filed on Sep. 26, 2019.

(51) Int. Cl.
*A61M 60/122* (2021.01)
*A61M 60/135* (2021.01)
*A61M 60/422* (2021.01)
*A61M 60/523* (2021.01)

(52) U.S. Cl.
CPC ........ *A61M 60/523* (2021.01); *A61M 60/135* (2021.01); *A61M 60/422* (2021.01); *A61M 2205/50* (2013.01)

(58) Field of Classification Search
CPC ................ A61M 60/50; A61M 60/562; A61M 2205/3334; A61M 2230/04
See application file for complete search history.

(56) References Cited

U.S. PATENT DOCUMENTS

| | | | |
|---|---|---|---|
| 7,997,854 B2 | 8/2011 | LaRose et al. | |
| 8,007,254 B2 | 8/2011 | LaRose et al. | |
| 8,419,609 B2 | 4/2013 | Shambaugh, Jr. et al. | |
| 8,512,013 B2 | 8/2013 | LaRose et al. | |
| 9,561,313 B2 | 2/2017 | Taskin | |
| 9,694,123 B2 | 7/2017 | Bourque et al. | |
| 10,010,662 B2 | 7/2018 | Wiesener et al. | |
| 10,159,775 B2 | 12/2018 | Voskoboynikov | |
| 2010/0222878 A1* | 9/2010 | Poirier | A61M 60/857 623/3.28 |
| 2011/0112354 A1 | 5/2011 | Nishimura | |

(Continued)

OTHER PUBLICATIONS

PCT/US2020/049134, The International Search Report and Written Opinion, mailed Dec. 4, 2020, 12 pages.

*Primary Examiner* — Michael J D'Abreu

(74) *Attorney, Agent, or Firm* — Shumaker & Sieffert, P.A.

(57) ABSTRACT

A control circuit for controlling a pump speed of a blood pump implanted in a patient including a processor in communication with the implanted blood pump, the processor having processing circuitry configured to reduce a pump speed relative to a standard set speed based on a timing of a systole phase of the patient, the systole phase including a first segment during which a ventricular pressure is at its greatest and a second segment occurring after the first segment during which the ventricular pressure is at its lowest, the pump speed being reduced during the second segment.

18 Claims, 5 Drawing Sheets

Decrease and increase in pump speed based on a flow threshold

(56) References Cited

U.S. PATENT DOCUMENTS

| | | |
|---|---|---|
| 2014/0275727 A1 | 9/2014 | Bonde et al. |
| 2014/0323796 A1* | 10/2014 | Medvedev .......... A61M 60/232 600/17 |
| 2015/0367048 A1 | 12/2015 | Brown et al. |
| 2018/0028738 A1 | 2/2018 | Brown et al. |
| 2018/0333525 A1 | 11/2018 | Medvedev et al. |
| 2019/0054222 A1 | 2/2019 | Reyes et al. |

* cited by examiner

BLOOD PUMP ALGORITHM FOR PREVENTING AND RESOLVING LEFT VENTRICULAR SUCTION THROUGH DYNAMIC SPEED RESPONSE

CROSS-REFERENCE TO RELATED APPLICATION

This application claims the benefit of U.S. Application Ser. No. 62/906,294, filed Sep. 26, 2019.

FIELD

The present technology is generally related to a method and system for preventing and/or resolving an adverse event associated with an implantable blood pump.

BACKGROUND

Implantable blood pumps are commonly used to assist the pumping action of a failing heart and typically include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. A known type of blood pump is a ventricular assist device ("VAD") with examples including, but not limited to, the HVAD® pump and the MVAD® pump manufactured by HeartWare, Inc. in Miami Lakes, Fla., USA.

To provide clinically useful assistance to the heart, blood pumps impel blood at a relatively substantial rate. However, blood pumps may be associated with one or more adverse events, such as suction, occlusion, or high differential pump pressure. Suction is an intermittent decrease in flow through the pump, otherwise known as a mismatch between the pump output and venous return. Suction typically occurs at the pump's inlet due to volumetric depletion within a heart chamber or due to a proximity between the pump's inlet and a myocardial structure. Occlusion is a sustained decrease in flow through the pump which may occur at the pump's inlet when the pump's inflow is sealed due to a proximity between the pump's inlet and a myocardial structure. Existing methods of controlling a blood pump fail to provide a mechanism for preventing adverse events or, when attempting to clear adverse events, negatively affect patient perfusion by decreasing the pump speed by an unsafe magnitude and/or duration that lasts throughout multiple phases of a patient's cardiac cycle.

SUMMARY

The techniques of this disclosure generally relate to a device, system, and method for altering a pump speed of an implantable blood pump during select segments of a cardiac cycle based on one or more flow parameters of the blood pump to prevent or clear an adverse event with minimal impact on patient profusion.

In one aspect, the present disclosure provides a control circuit for controlling a pump speed of a blood pump implanted in a patient including a processor in communication with the implanted blood pump, the processor having processing circuitry configured to reduce a pump speed relative to a standard set speed based on a timing of a systole phase of the patient, the systole phase including a first segment during which systolic pressure is at its greatest and a second segment occurring after the first segment during which systolic pressure is at its lowest, the pump speed being reduced during the second segment.

In another aspect, the disclosure provides the second segment of the systole phase including an end portion, and wherein the processing circuitry is configured to reduce the pump speed from the standard set speed to a reduced speed during the end portion.

In another aspect, the disclosure provides the processing circuitry being configured to establish a predetermined flow threshold associated with the blood pump; determine a current flow value through the blood pump; correlate the current flow value to the predetermined flow threshold; and reduce the pump speed from the standard set speed to a reduced speed when the current flow value is below the predetermined flow threshold.

In another aspect, the disclosure provides the processing circuitry being further configured to increase the pump speed from the reduced speed to the standard set speed when the current flow value is above the predetermined flow threshold, and wherein the current flow value being above the flow threshold is associated with the first segment of the systole phase.

In another aspect, the disclosure provides the processing circuitry being further configured to automatically increase the pump speed from the reduced speed to the standard set speed when the current flow value crosses and exceeds the predetermined flow threshold, and wherein the current flow value exceeding the flow threshold is associated with the cardiac phase being within the first segment of the systole phase.

In another aspect, the disclosure provides the processing circuitry being further configured to increase the pump speed from the reduced speed to the standard set speed after a predetermined time interval.

In another aspect, the disclosure provides the processing circuitry being further configured to determine one from the group consisting of a presence and an absence of an adverse physical state of the patient, and reduce the pump speed from the standard set speed to the reduced speed in the absence of the adverse physical state.

In another aspect, the disclosure provides the processing circuitry being further configured to periodically reduce the pump speed relative to the standard set speed during the second segment of the systole phase on a non-routine basis.

In another aspect, the disclosure provides the processing circuitry being further configured to alter the pump speed relative to the standard set speed in the presence of an adverse physical state.

In another aspect, the disclosure provides the adverse physical state being a suction condition.

In one aspect, the disclosure provides a control system for controlling a blood pump implanted in a patient, the patient having a cardiac cycle including a cardiac phase having a first segment during which a ventricular pressure is at a maximum pressure and a second segment during which the ventricular pressure is a minimum pressure for the cardiac phase, and the control system including the blood pump having an impeller configured to rotate at a pump speed; and a control circuit including processor in communication with the blood pump, the processor having processing circuitry configured to reduce the pump speed from a standard set speed associated with a normal operation of the blood pump during the first segment of the cardiac phase to a reduced speed based on a timing of the second segment of the cardiac phase.

In another aspect, the disclosure provides the second segment of the cardiac phase including an end portion, and the processing circuitry is configured to determine a timing of the end portion and reduce the pump speed from the standard set speed to the reduced speed during the end portion.

In another aspect, the disclosure provides the cardiac phase being a systole phase, and the processing circuitry is configured to periodically reduce the pump speed relative to the standard set speed during the end portion of the systole phase.

In another aspect, the disclosure provides the cardiac phase being a systole phase, and the processing circuitry is configured to establish a predetermined flow threshold associated with the blood pump; determine a current flow value through the blood pump; correlate the current flow value to the predetermined flow threshold; and decrease the pump speed from the standard set speed to a reduced speed relative to the standard set speed when the current flow value is below the predetermined flow threshold.

In another aspect, the disclosure provides the processing circuitry being further configured to increase the pump speed from the reduced speed to the standard set speed when the current flow value is above the predetermined flow threshold.

The control system of Claim 15, wherein the processing circuitry is further configured to automatically increase the pump speed from the reduced speed to the standard set speed when the current flow value crosses and exceeds the predetermined flow threshold, and wherein the current flow value exceeding the flow threshold is associated with the cardiac phase being within the first segment of the systole phase.

In another aspect, the disclosure provides the processing circuitry being further configured to increase the pump speed from the reduced speed to the standard set speed after a predetermined time interval.

In another aspect, the disclosure provides the processing circuitry being further configured to determine a presence or an absence of an adverse physical state of the patient and decrease the pump speed from the standard set speed to the reduced speed in the absence of the adverse physical state.

In another aspect, the disclosure provides the processing circuitry being further configured to alter the pump speed relative to the standard set speed in the presence of the adverse physical state, and the adverse physical state is a suction condition.

In one aspect, the disclosure provides a control circuit for controlling a pump speed of a blood pump implanted in a patient, the patient having a cardiac cycle including a systole phase having an end portion during which a systolic pressure of the patient is at a maximum for the patient, and the control circuit including a processor in communication with the implanted blood pump, the processor having processing circuitry configured to determine a standard set speed of the blood pump; establish a predetermined flow threshold associated with a fluid flowing in the blood pump; determine a current flow value through the blood pump; correlate the current flow value to the predetermined flow threshold; decrease the pump speed from the standard set speed to a reduced speed relative to the standard set speed during the end portion of the systole phase based on when the current flow value is below the predetermined flow threshold; and increase the pump speed from the reduced speed to the standard set speed at the systole phase and based on one of the group consisting of a predetermined time interval and when the current flow value exceeds the predetermined flow threshold.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
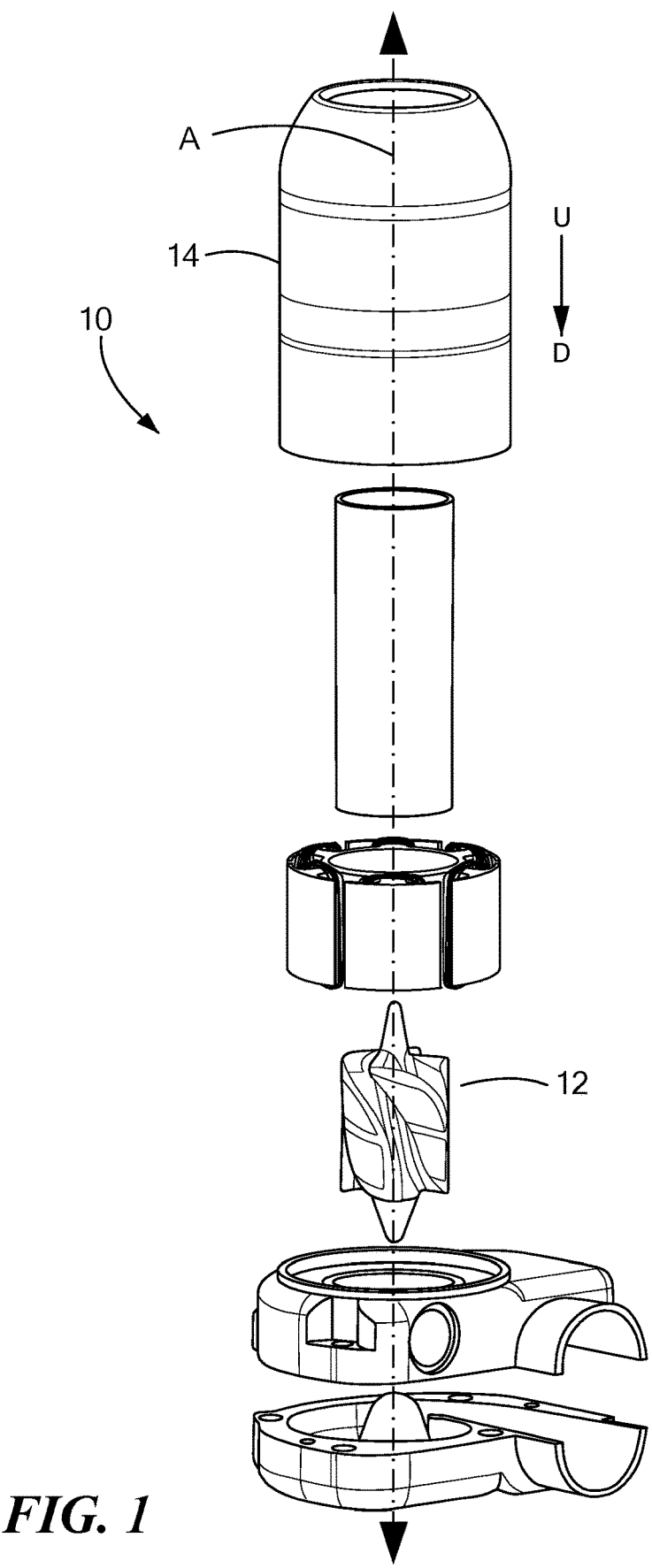
FIG. 1 is a disassembled view of an implantable blood pump.

Before describing in detail exemplary embodiments, it is noted that the configurations reside primarily in combinations of device and system components and method steps related to preventing or clearing an adverse event associated with an implantable blood pump. Accordingly, the device, system, and method components have been represented where appropriate by conventional symbols in the drawings, showing only those specific details that are pertinent to understanding the configurations of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate, and modifications and variations are possible of achieving the electrical and data communication.

Referring now to the drawings in which like reference designators refer to like elements there is shown in FIG. 1 a disassembled view of an exemplary implantable blood pump 10 configured to be implanted within a patient, such as a human or animal patient. The blood pump 10 may be, without limitation, the HVAD® Pump or the MVAD® Pump, having a movable element, such as an impeller 12 or a rotor, configured to rotate and impel blood from the heart to the rest of the body. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
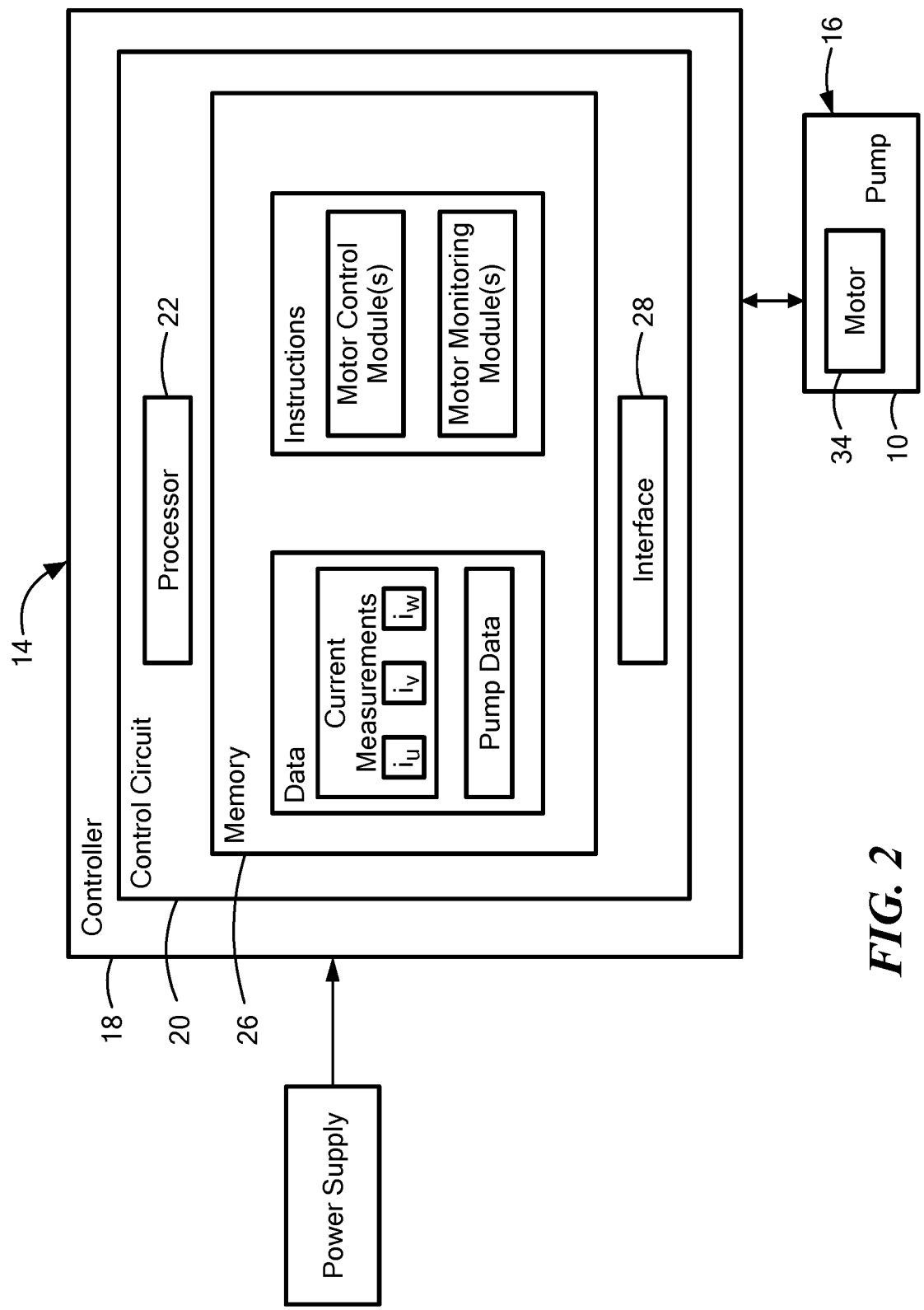
FIG. 2 is a block diagram of a system for controlling a pump speed of the blood pump of FIG. 1.

FIG. 2 is a block diagram of an exemplary system 14 for controlling a pump speed and/or other operations of the implantable blood pump 10 when the blood pump 10 is in communication with the system 14. The blood pump 10 includes a motor 16 therein and may be a separate component or form part of the system 14. In one example, the system 14 includes a controller 18 having a control circuit 20 and a processor 22 including processing circuitry 24 configured to perform the operations of the blood pump 10. The system 14 may also include a memory 26 and an interface 28, the memory 26 being configured to store information accessible by the processor 22, including instructions executable by the processing circuitry 24 and/or data that may be retrieved, manipulated or stored by the processor 22. Such instructions and/or data include that which is used to control the pump speed.

Figure 3:
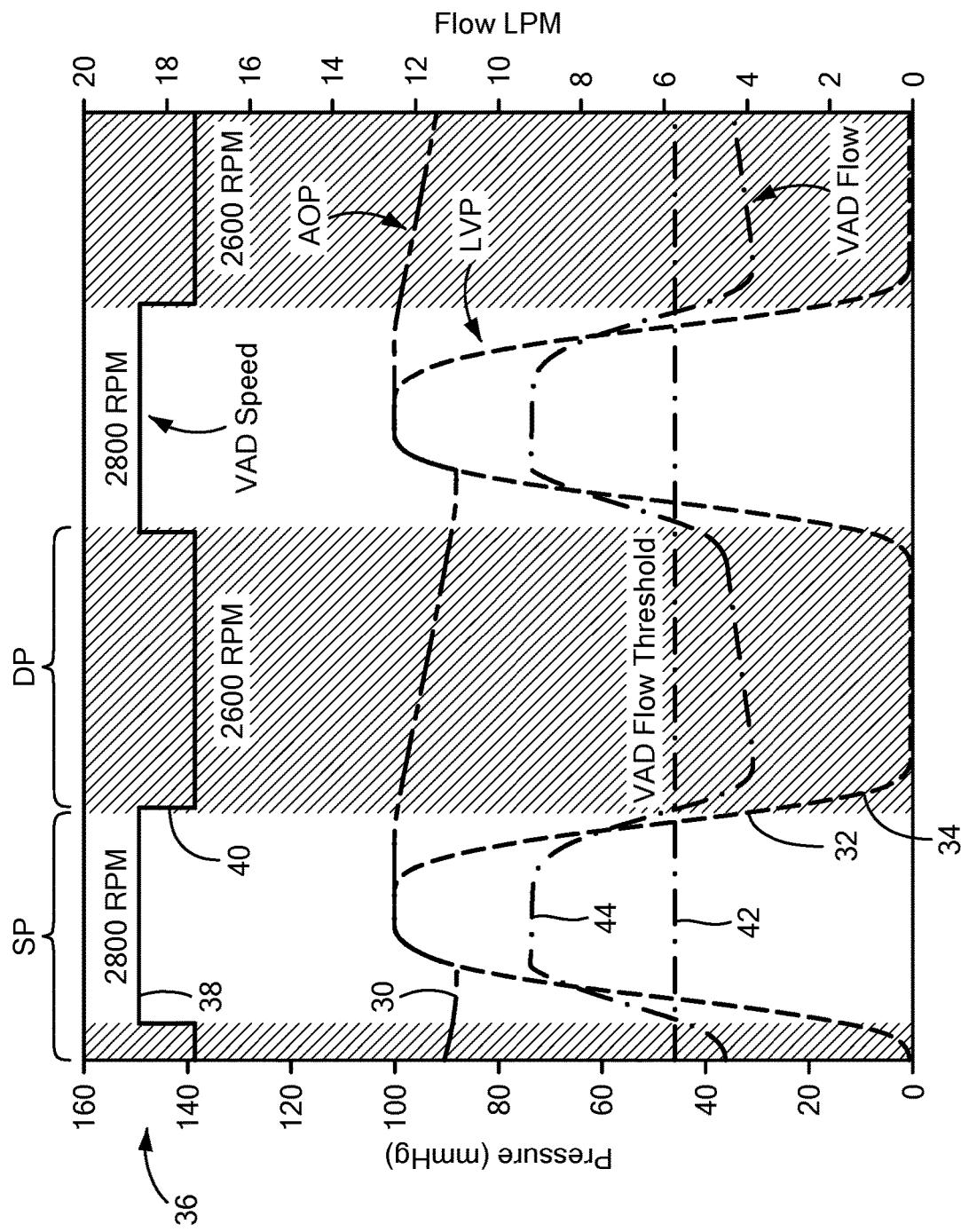
FIG. 3 is a diagram showing changes in the pump speed of the blood pump of FIG. 1 relative to variations in an aortic pressure and a ventricular pressure of a patient and a plurality of flow parameters of the blood pump.

FIG. 3 is a diagram showing changes in the pump speed 36 relative to variations in an aortic pressure and a ventricular pressure of a patient and flow parameters of the blood pump 10. The patient's aortic pressure is represented by an aortic pressure waveform AOP and the ventricular pressure is represented by a ventricular pressure waveform LVP with both waveforms plotted relative to pressure (mmHG) as a Y axis value.

The aortic pressure and the ventricular pressure change as the patient's cardiac cycle undergoes a systole phase SP and a diastole phase DP. During the systole phase SP when the heart contracts, the ventricular pressure increases to open the aortic valve and eject blood from the heart into the patient's aorta and pulmonary trunk. The force of blood ejected into the aorta increases the pressure in the aorta to a maximum pressure commonly referred to as a systolic pressure. During the diastole phase, the ventricular pressure is a minimum or lowest pressure as the heart relaxes and fills with blood.

The systole phase SP includes a first segment 30 during which the ventricular pressure increases and is at its greatest pressure and a second segment 32, occurring after the first segment 30, during which the ventricular pressure is descending to its lowest pressure for the systolic phase. In other words, during the first segment 30 and the second segment 32 of the systole phase, the ventricular pressure is at a maximum pressure and a minimum pressure for the systolic phase, respectively. FIG. 3 shows that when the ventricular pressure is at its greatest, the aortic pressure is equal to the ventricular pressure. The second segment 32 of the systole phase SP includes an end portion 34 characterized as being when the ventricular pressure is between 20 mmHg and at least 1 mmHg and thus prior to the beginning of the diastole phase which occurs after the second segment 32 of the systole phase SP.

The processing circuitry 24 is configured to reduce the pump speed 36 relative to a standard set speed 38 based on a timing of the systole phase SP, such as during the end portion 34 of the second segment 32, to lower the shut off pressure in attempt to clear an adverse event without significantly impacting patient perfusion. In other words, reducing the pump speed 36 during the end portion 34 of the systole phase SP promotes the pumping of fluid through the blood vessels. The adverse event may be a suction condition or another condition negatively impacting pump performance and thus being hazardous for the patient. The system 14 is not limited to reducing the pump speed 36 during the systole phase, rather, the processing circuitry 24 may be configured to reduce the pump speed 36 during the diastole phase of the cardiac cycle as well.

The standard set speed 38 may be a normal daily or standard speed for the patient and the blood pump 10. FIG. 3 depicts the standard set speed 38 as being within a 200 RPM range of 2800 RPM and the reduced pump speed 40 as being within a 200 RPM range of 2600 RPM, however, such speeds are exemplary and may vary according to the patient and the blood pump 10. The magnitude of speed reduction may be determined by a standard value customary for multiple patients or specific to the individual patient.

In one example, the processing circuitry 24 is configured to determine a presence or absence of the adverse event and reduce the pump speed 36 from the standard set speed 38 to the reduced speed 40 in the absence of the adverse event, such as on a non-routine basis or periodically in attempt to prevent an adverse event from occurring. The periodic activation of the speed reduction may occur at the end portion 34 of the systole phase SP over various hours, days, and/or intervals. In addition to that described above, reducing the pump speed 36 at the end portion 34 of the systole phase SP allows the patient's ventricle to remain relatively fuller during the end of the systole phase SP to prevent volumetric depletion within the heart chamber and thus decrease the chances of the adverse event without significantly impacting patient perfusion.

FIG. 3 depicts the flow parameters associated with the blood pump 10 measured relative to flow in liters per minute as a Y axis value. Select changes in one or more of the flow parameters may trigger the processing circuitry 24 to alter the pump speed 36 relative thereto. Further, the changes in the flow parameters correlate to the systole phase and the diastole phase of the cardiac cycle.

In one example, the processing circuitry 24 is configured to establish a predetermined flow threshold 42 associated with the blood pump 10, determine a current flow value 44 through the blood pump 10, and correlate the current flow value 44 to the predetermined flow threshold 42. The predetermined flow threshold 42 or flow threshold 42 may be established using an instantaneous flow algorithm or another determination method. The current flow value 44 is shown in the form of a current flow value waveform representing a real-time or estimated value of the fluid, such as blood, flowing through the blood pump 10.

The processing circuitry 24 is configured to reduce the pump speed 36 from the standard set speed 38 to the reduced speed 40 when the current flow value 44 is below the flow threshold 42, for example when the current flow value 44 crosses the flow threshold 42 in a descending direction toward a zero value. The current flow value 44 crossing the flow threshold 42 in the descending direction correlates to the end portion 34 of the second segment 32 of the systole phase SP.

Further, the processing circuitry 24 may be configured to automatically increase the pump speed 36 from the reduced speed 40 to the standard set speed 38 when the current flow value 44 is above the flow threshold 42, for example when the current flow value 44 crosses to exceed the flow threshold 42. The current flow value 44 exceeding the flow threshold 42 typically correlates to the first segment 30 of the systole phase SP. As such, the duration of the speed decrease is configured to occur within only a portion of the cardiac cycle, e.g., the diastole phase, to promote patient perfusion.

Figure 4:
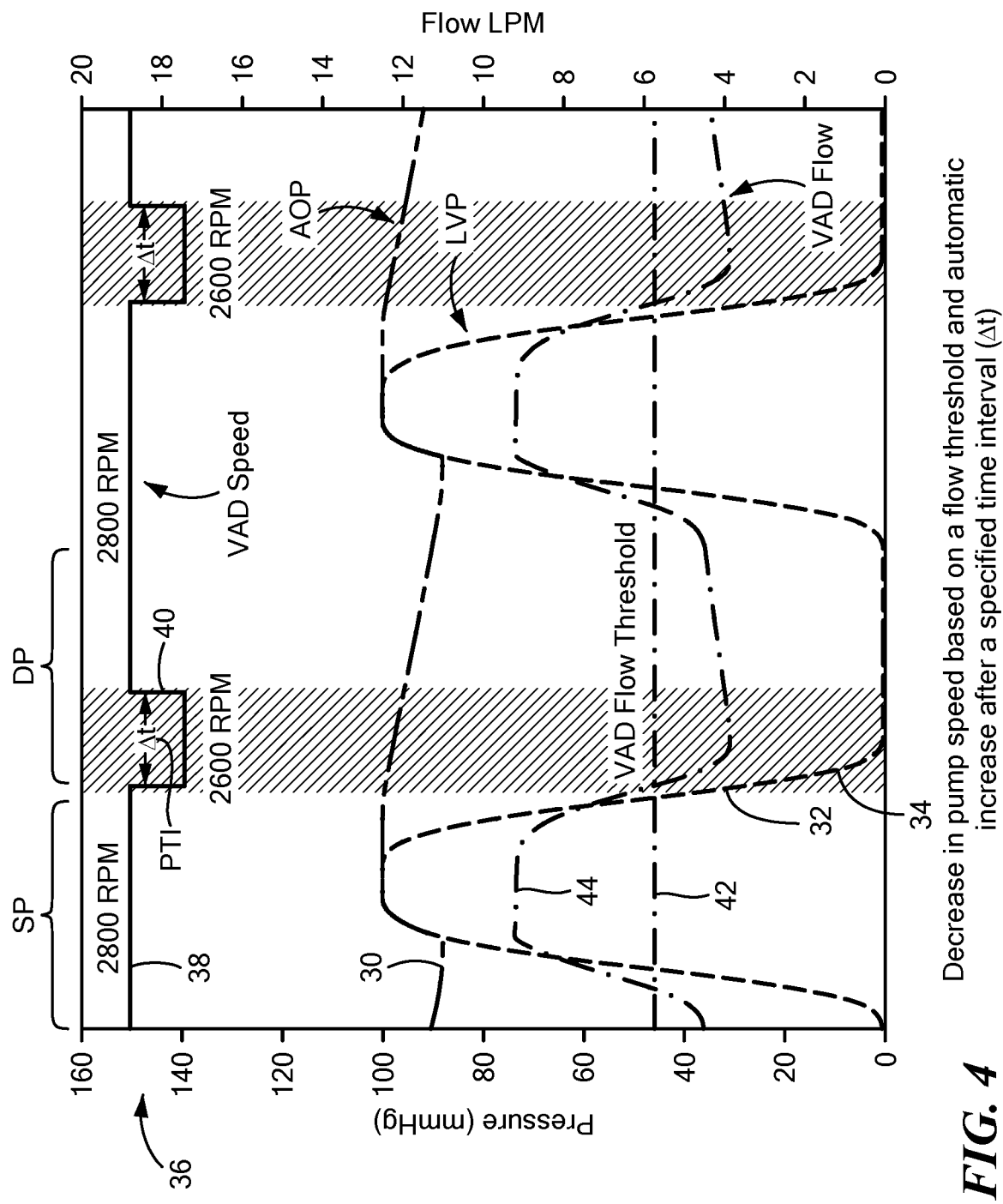
FIG. 4 is a diagram showing the parameters similar to FIG. 3, with the exception of the pump speed being altered by the system of FIG. 2 after a predetermined time period.

FIG. 4 is a diagram representing the processing circuitry 24 configured to increase the pump speed 36 after a predetermined time interval PTI, rather than when the current flow value 44 exceeds the predetermined flow threshold 42. The duration of the predetermined time interval may vary depending upon the patient and is shown in FIG. 4 as occurring within the diastole phase DP for exemplary purposes. Similar to FIG. 3, FIG. 4 shows changes in the pump speed 36 relative to variations in the aortic pressure and the ventricular pressure of the patient and flow parameters of the blood pump 10. The reduction of the pump speed 36 in FIG. 4 occurs in the same manner as described above with respect to FIG. 3, such as when the current flow value 44 crosses the flow threshold 42 in the descending direction toward the zero value at the end portion 34 of the systole phase SP.

Figure 5:
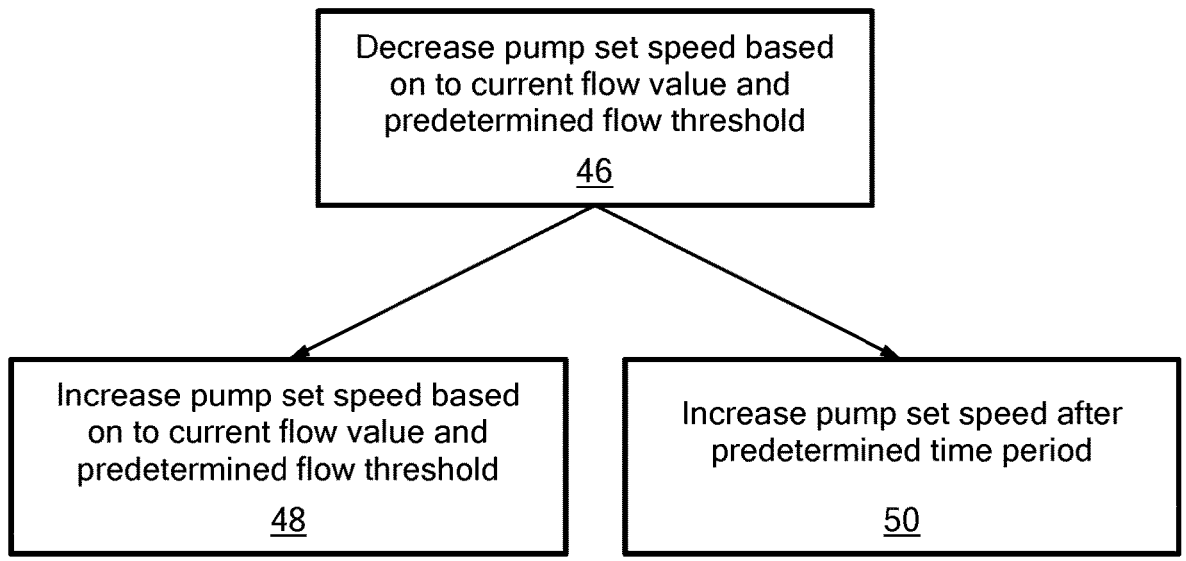
FIG. 5 is a flow diagram showing a method of controlling the pump speed of the blood pump of FIG. 1 to prevent or clear an adverse event.

FIG. 5 is a flow diagram showing a method of altering the pump speed 36 of the blood pump 10 in accordance with a timing of the patient's cardiac cycle to prevent or clear an adverse event. The method may be carried out by the system 14 or another system configured to communicate with the blood pump 10. For example, the processing circuitry 24 of the system 14 may be configured to perform the method steps automatically and/or in combination with manual inputs. FIG. 5 shows one or more method steps which may be executed in a different order or which may deviate from that which is shown.

In one example, the method begins at step 46 including the processing circuitry 24 decreasing the pump speed 36 from the standard set speed 38 to the reduced speed 40 relative to the standard set speed 38 during the second segment 32, such as the end portion 34, of the systole phase of the cardiac cycle. The decrease in the pump speed 36 is triggered when the current flow value 44 crosses the predetermined flow threshold 42 to fall therebelow. At step 48, the processing circuitry 24 increases the pump speed from the reduced speed 40 to the standard set speed 38 when the current flow value 44 crosses to exceed the predetermined flow threshold 42. In the alternative, the method may proceed from step 46 to step 50 wherein the speed increase occurs after a predetermined time interval without taking into account the current flow value 44 and the predetermined flow threshold 42. In one or more examples, although the speed decrease begins at the end portion 34 of the systole phase, the duration of the speed decrease lasts only during the diastole phase which directly precedes the systole phase during which the pump speed 36 decrease occurred.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A controller configured to control a pump speed of a blood pump, the controller comprising:
   a processor configured to communicate with the blood pump, the processor having processing circuitry configured to:
      determine a current flow value, wherein the current flow value represents a value of fluid flowing through the blood pump;
      compare the current flow value to a predetermined flow threshold; and
      reduce a pump speed of the blood pump to a reduced speed when the current flow value is below the predetermined flow threshold,
   wherein the predetermined flow threshold corresponds to a second segment of a systole phase of a patient, the systole phase including a first segment during which a ventricular pressure is at its greatest and the second segment occurring after the first segment during which the ventricular pressure is at its lowest, the pump speed being reduced during the second segment.

2. The controller of claim 1, wherein the processing circuitry is configured to reduce the pump speed to the reduced speed by at least reducing the pump speed from a standard set speed to the reduced speed, and wherein the processing circuitry is further configured to increase the pump speed from the reduced speed to the standard set speed when the current flow value is above the predetermined flow threshold, and wherein the current flow value being above the flow threshold is associated with the first segment of the systole phase.

3. The controller of claim 2, wherein the processing circuitry is further configured to automatically increase the pump speed from the reduced speed to the standard set speed when the current flow value crosses and exceeds the predetermined flow threshold, and wherein the current flow value exceeding the flow threshold is associated with a cardiac phase being within the first segment of the systole phase.

4. The controller of claim 1, wherein the processing circuitry is configured to reduce the pump speed to the reduced speed by at least reducing the pump speed from a standard set speed to the reduced speed, and wherein the processing circuitry is further configured to alter the pump speed relative to the standard set speed in a presence of an adverse physical state.

5. The controller of claim 4, wherein the adverse physical state is a suction condition.

6. The controller of claim 1, wherein the second segment of the systole phase includes an end portion, and wherein the processing circuitry is configured to reduce the pump speed from a standard set speed to the reduced speed during the end portion.

7. The controller of claim 1, wherein the processing circuitry is configured to reduce the pump speed to the reduced speed by at least reducing the pump speed from a standard set speed to the reduced speed, and wherein the processing circuitry is further configured to increase the pump speed from the reduced speed to the standard set speed after a predetermined time interval.

8. The controller of claim 1, wherein the processing circuitry is configured to reduce the pump speed to the reduced speed by at least reducing the pump speed from a standard set speed to the reduced speed, and wherein the processing circuitry is further configured to determine a presence or an absence of an adverse physical state of the patient, and reduce the pump speed from the standard set speed to the reduced speed in the absence of the adverse physical state.

9. The controller of claim 1, wherein the processing circuitry is configured to reduce the pump speed to the reduced speed by at least reducing the pump speed from a standard set speed to the reduced speed, and wherein the processing circuitry is further configured to periodically reduce the pump speed relative to the standard set speed during the second segment of the systole phase on a non-routine basis.

10. A control system for controlling a blood pump implanted in a patient, the blood pump including an impeller configured to rotate at a pump speed, the patient having a cardiac cycle including a cardiac phase having a first segment during which a ventricular pressure is at a maximum pressure and a second segment during which the ventricular pressure is a minimum pressure, and the control system comprising:
a control circuit including a processor in communication with the blood pump, the processor having processing circuitry configured to:
determine a current flow value, wherein the current flow value represents a value of fluid flowing through the blood pump;
compare the current flow value to a predetermined flow threshold; and
reduce the pump speed from a standard set speed associated with operation of the blood pump during the first segment of the cardiac phase to a reduced speed when the current value is below the predetermined flow threshold.

11. The control system of claim 10, wherein the second segment of the cardiac phase includes an end portion, and the processing circuitry is configured to determine a timing of the end portion and reduce the pump speed from the standard set speed to the reduced speed during the end portion.

12. The control system of claim 11, wherein the cardiac phase is a systole phase, and the processing circuitry is configured to periodically reduce the pump speed relative to the standard set speed during the end portion of the systole phase.

13. The control system of claim 10, wherein the processing circuitry is further configured to:
increase the pump speed from the reduced speed to the standard set speed when the current flow value is above the predetermined flow threshold.

14. The control system of claim 13, wherein the processing circuitry is further configured to automatically increase the pump speed from the reduced speed to the standard set speed when the current flow value crosses and exceeds the predetermined flow threshold, and wherein the current flow value exceeding the flow threshold is associated with the cardiac phase being within the first segment of the cardiac phase.

15. The control system of claim 10, wherein the processing circuitry is further configured to increase the pump speed from the reduced speed to the standard set speed after a predetermined time interval.

16. The control circuit of claim 10, wherein the processing circuitry is further configured to:
determine a presence or an absence of an adverse physical state of the patient, and decrease the pump speed from the standard set speed to the reduced speed in the absence of the adverse physical state.

17. The control circuit of claim 16, wherein the processing circuitry is further configured to:
alter the pump speed relative to the standard set speed in the presence of the adverse physical state, and the adverse physical state is a suction condition.

18. A control circuit for controlling a pump speed of a blood pump implanted in a patient, the patient having a cardiac cycle including a systole phase having an end portion during which a systolic pressure of the patient is at a maximum for the patient, the control circuit comprising:
a processor in communication with the implanted blood pump, the processor having processing circuitry configured to:
determine a standard set speed of the blood pump;
establish a predetermined flow threshold associated with a fluid flowing in the blood pump;
determine a current flow value, wherein the current flow value represents a value of the fluid flowing in the blood pump;
compare the current flow value to the predetermined flow threshold;
decrease the pump speed from the standard set speed to a reduced speed relative to the standard set speed during the end portion of the systole phase based on when the current flow value is below the predetermined flow threshold; and increase the pump speed from the reduced speed to the standard set speed at the systole phase and based on one of the group consisting of a predetermined time interval and when the current flow value is above the predetermined flow threshold.

\* \* \* \* \*